(12) United States Patent
Takeuchi et al.

(10) Patent No.: US 10,781,416 B2
(45) Date of Patent: Sep. 22, 2020

(54) CONNECTION MECHANISM

(71) Applicant: SINFONIA TECHNOLOGY CO., LTD., Minato-ku (JP)

(72) Inventors: Haruki Takeuchi, Minato-ku (JP); Yoshimasa Suda, Minato-ku (JP)

(73) Assignee: SINFONIA TECHNOLOGY CO., LTD., Minato-ku (JP)

( * ) Notice: Subject to any disclaimer, the term of this patent is extended or adjusted under 35 U.S.C. 154(b) by 198 days.

(21) Appl. No.: 15/766,037

(22) PCT Filed: Oct. 4, 2016

(86) PCT No.: PCT/JP2016/079496
§ 371 (c)(1),
(2) Date: Apr. 5, 2018

(87) PCT Pub. No.: WO2017/061430
PCT Pub. Date: Apr. 13, 2017

(65) Prior Publication Data
US 2018/0282675 A1    Oct. 4, 2018

(30) Foreign Application Priority Data
Oct. 7, 2015  (JP) .................................. 2015-199077

(51) Int. Cl.
*G01N 1/00*   (2006.01)
*C12M 1/12*   (2006.01)
(Continued)

(52) U.S. Cl.
CPC .............. *C12M 1/12* (2013.01); *C12M 23/02* (2013.01); *C12M 23/44* (2013.01); *C12M 37/04* (2013.01)

(58) Field of Classification Search
CPC ....................................................... G01N 1/00
See application file for complete search history.

(56) References Cited

U.S. PATENT DOCUMENTS 4,494,586 A       1/1985   Picard
6,969,497 B2 *   11/2005   Sacca ................... A61L 2/0005
                                                                  312/1
(Continued)

FOREIGN PATENT DOCUMENTS

JP    51-049520 A    11/1976
JP    57-160098 A    10/1982
(Continued)

OTHER PUBLICATIONS

International Search Report dated Jan. 10, 2017 in PCT/JP2016/079496, filed on Oct. 4, 2016.

*Primary Examiner* — Jyoti Nagpaul
(74) *Attorney, Agent, or Firm* — Oblon, McClelland, Maier & Neustadt, L.L.P.

(57) ABSTRACT

A connection mechanism includes two connection parts. Each connection part includes a first flange including a through hole and an attaching portion by which the first flange is attached to a partial wall portion while the through hole faces an opening. The attaching portion includes: a vertical adjuster which adjusts the attaching position of the first flange so that a surface of the first flange, which is opposite to a surface of the first flange facing the partial wall portion, is vertical; and a rotation adjuster which adjusts the attaching position of the first flange about a horizontal axis passing the center of the through hole and extending in the thickness direction. The attaching position of a first flange can be individually adjusted.

4 Claims, 14 Drawing Sheets

(51) Int. Cl.
*C12M 3/00* (2006.01)
*C12M 1/00* (2006.01)

(56) References Cited

U.S. PATENT DOCUMENTS

2017/0137765 A1 5/2017 Tamura
2017/0137770 A1 5/2017 Sakamoto et al.

FOREIGN PATENT DOCUMENTS

| JP | 2010-195432 A | 9/2010 |
| JP | 2012-147685 A | 8/2012 |
| JP | 2016-013062 A | 1/2016 |
| WO | WO 2015/190502 A1 | 12/2015 |

* cited by examiner

CIRCUMFERENTIAL DIRECTION

CIRCUMFERENTIAL DIRECTION

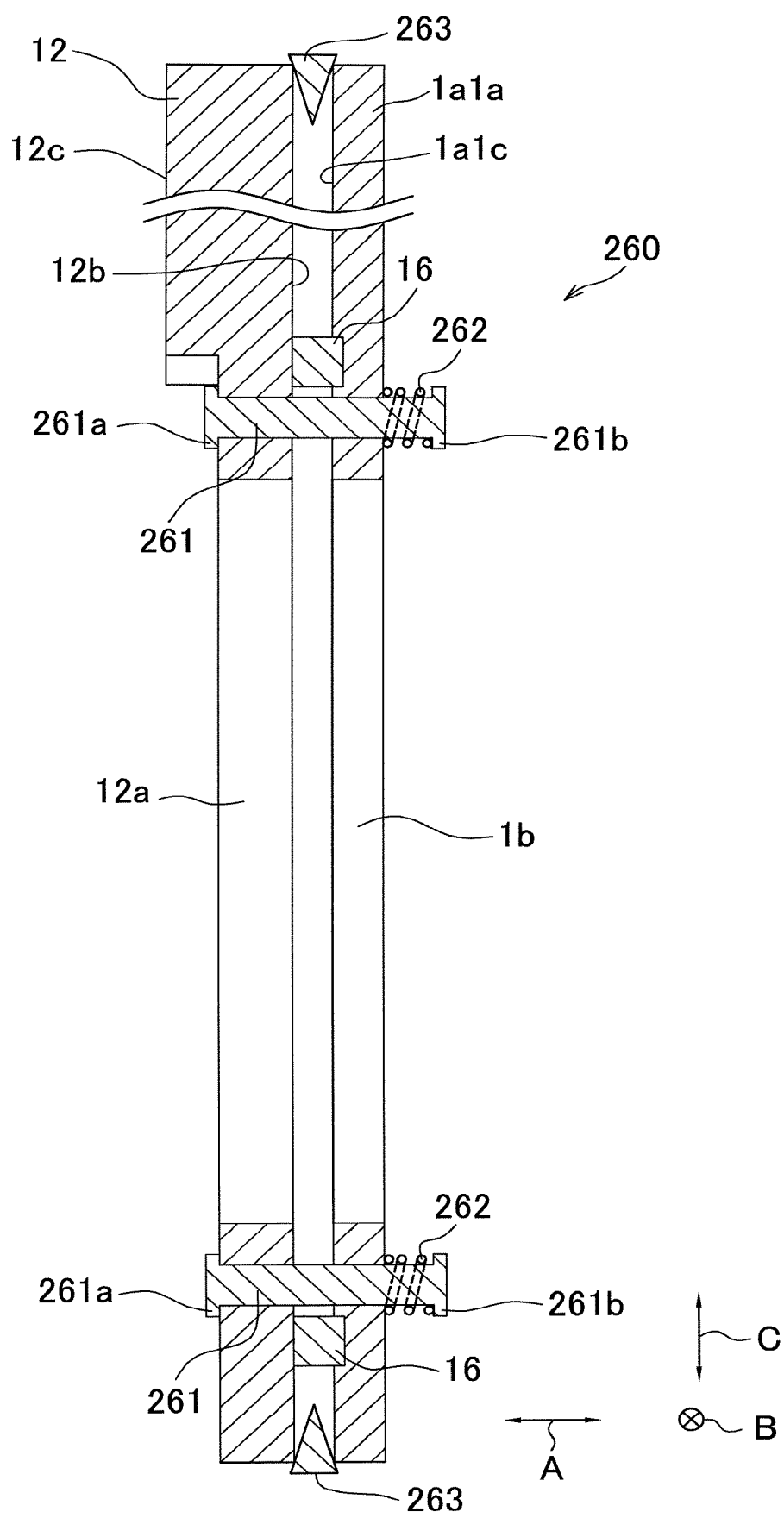

CONNECTION MECHANISM

TECHNICAL FIELD

The present invention relates to a connection mechanism including connection parts by which housings each having an internal space are connected to each other.

BACKGROUND ART

Patent Literature 1 recites a cell culture processing system including a first processing apparatus (first housing) having a sealed space shielded from the external environment, a plurality of second processing apparatuses (second housings) each having a sealed space shielded from the external environment, and a plurality of attaching-detaching units (junctions) which are provided on a side face of the first processing apparatus in order to attach and detach the second processing apparatuses to and from the first processing apparatus. As the first processing apparatus is connected to the second processing apparatuses by the attaching-detaching units, the sealed spaces of these processing apparatuses form a single continuous sealed space.

CITATION LIST

Patent Literatures

Patent Literature 1: Japanese Unexamined Patent Publication No. 2012-147685

SUMMARY OF INVENTION

Technical Problem

The first processing apparatus of the cell culture processing system of Patent Literature 1 described above is provided with the attaching-detaching units. While Patent Literature 1 above does not detail the attaching-detaching units, when, for example, the attaching-detaching units are formed integrally with the first processing apparatus, i.e., when a side wall of the casing of the first processing apparatus and constituting members of each attaching-detaching unit are cut out from a single member, variation in accuracy between the components is restrained, with the result that a positional error between the attaching-detaching units on the first processing apparatus is extremely small. On this account, when the casing of the first processing apparatus is accurately installed, variation between the attaching-detaching units is small. However, the cut out from a single member requires large manufacturing equipment and significantly high manufacturing cost.

Under this circumstance, the inventors of the present invention tried to decrease the manufacturing cost by attaching, to a side wall of a first housing defining an internal space, flanges which were for connecting a second housing and were manufactured independently from the side wall. As a result of this, the inventors found the following problem. When flanges are attached to a side wall of the first housing, there is an attachment error between the flanges. On this account, even if the first housing is accurately installed, the attaching position of each flange about a horizontal axis passing the center of a through hole of the flange (i.e., the through hole connected to the internal space) and the attaching position of each flange at which the surface of the flange opposite to the surface facing the side wall of the first housing is vertical are disadvantageously different between the flanges.

An object of the present invention is therefore to provide a connection mechanism which allows the attaching position of a first flange to be individually adjustable.

Solution to Problem

A connection mechanism of the present invention includes: a plurality of connection parts which connect a first housing including at least one first side wall defining an internal space and a plurality of first openings formed in the first side wall to a second housing including at least one second side wall defining an internal space and a second opening formed in the second side wall, the connection parts causing one of the first openings to communicate with the second opening, each of the connection parts including: a first flange which includes a first through hole penetrating the first flange in a thickness direction and is connected to the second housing when the first through hole faces the second opening; and an attaching portion which attaches the first flange to the first side wall when the first through hole faces the first opening. The attaching portion includes at least one of a first adjuster adjusting an attaching position of the first flange to cause an opposite surface of the first flange, which is opposite to a surface of the first flange facing the first side wall, to be vertical or a second adjuster adjusting an attaching position of the first flange about a horizontal axis which passes the center of the first through hole and extends along the thickness direction.

According to this arrangement, when the attaching portion includes the first adjuster, it is possible to adjust the opposite surface of the first flange to be vertical in each connection part when the opposite surface of the first flange is not vertical when the first housing is installed. When the attaching portion includes the second adjuster, a positional deviation of the first flange about the horizontal axis, which occurs when the first housing is installed, is adjustable at each connection part. Because the attaching position of the first flange is individually adjustable in this way, a difference in the attaching position of the first flange between the connection parts is decreased.

In the present invention, each of the connection parts further includes an annular elastic sealing member which is provided between the first flange and the first side wall to surround the first through hole and the first opening. The first adjuster preferably includes: a plurality of first screws which are provided around the first through hole of the first flange to determine the upper limit of a separation distance between the first flange and the first side wall within a range of elastic deformation of the sealing member; and a plurality of second screws which are provided around the first through hole of the first flange to adjust the attaching position of the first flange by changing the separation distance so that the opposite surface of the first flange is vertical, the separation distance changed by the second screws being equal to or shorter than the upper limit determined by the first screws. This arrangement makes it possible to adjust the attaching position of the first flange in such a way that the opposite surface of the first flange is vertical while the airtightness between the first flange and the first side wall is maintained.

The present invention is preferably arranged such that, the second adjuster includes: a plate which faces an inner circumferential surface of the first opening and an inner circumferential surface of the first through hole and is attached to the inner circumferential surface of the first opening; and an adjusting screw which is provided to face the inner circumferential surface of the first through hole and adjusts the attaching position of the first flange about the horizontal axis by changing a separation distance between the plate and the inner circumferential surface of the first through hole. This makes it possible to adjust the attaching position of the first flange about the horizontal axis.

In the present invention, the first flange is circular in shape, and each of the connection parts further includes: a movable member supported by a peripheral end portion of the first flange to be movable along the peripheral end portion; and a circular second flange which includes a second through hole penetrating the second flange in the thickness direction and is attached to the second side wall of the second housing when the second through hole faces the second opening. Furthermore, preferably, a plurality of protrusions are formed on an outer circumference side face of the second flange to protrude in a direction along the diameter of the second flange, the movable member includes a protruding portion which protrudes away from the first housing as compared to the opposite surface of the first flange, and the protruding portion includes a plurality of press portions which are engaged with the protrusions to press the second flange onto the first flange when the movable member is moved along the peripheral end portion while the opposite surface of the first flange faces an opposite surface of the second flange, which is opposite to a surface of the second flange facing the second side wall. With this arrangement, when the first housing is connected to the second housing, the connection is made while the flanges are closely in contact with each other, as the movable member is rotated along the peripheral end portion of the first flange.

The present invention is preferably arranged such that, each of the connection parts further includes an annular elastic sealing member which is provided between the first flange and the second flange to surround the first through hole and the second through hole. With this, airtightness between the first flange and the second flange is effectively maintained.

Advantageous Effects of Invention

With the connection mechanism of the present invention, when the attaching position of the first flange attached to the first side wall is adjustable about the horizontal axis, a positional deviation of the first flange about the horizontal axis, which occurs when the first housing is installed, is adjustable at each connection part. Furthermore, when the attaching position of the first flange attached to the first side wall is adjustable to arrange the opposite surface of the first flange to be vertical, it is possible to adjust the opposite surface of the first flange to be vertical in each connection part when the opposite surface of the first flange is not vertical when the first housing is installed. Because the attaching position of the first flange is individually adjustable in this way, a difference in the attaching position of the first flange between the connection parts is decreased.

BRIEF DESCRIPTION OF DRAWINGS

FIG. 13 shows a modification of a vertical adjuster.

DESCRIPTION OF EMBODIMENTS

The following will describe a culture apparatus 100 which employs a connection mechanism of an embodiment of the present invention, with reference to FIG. 1 to FIG. 12B.

Figure 1:
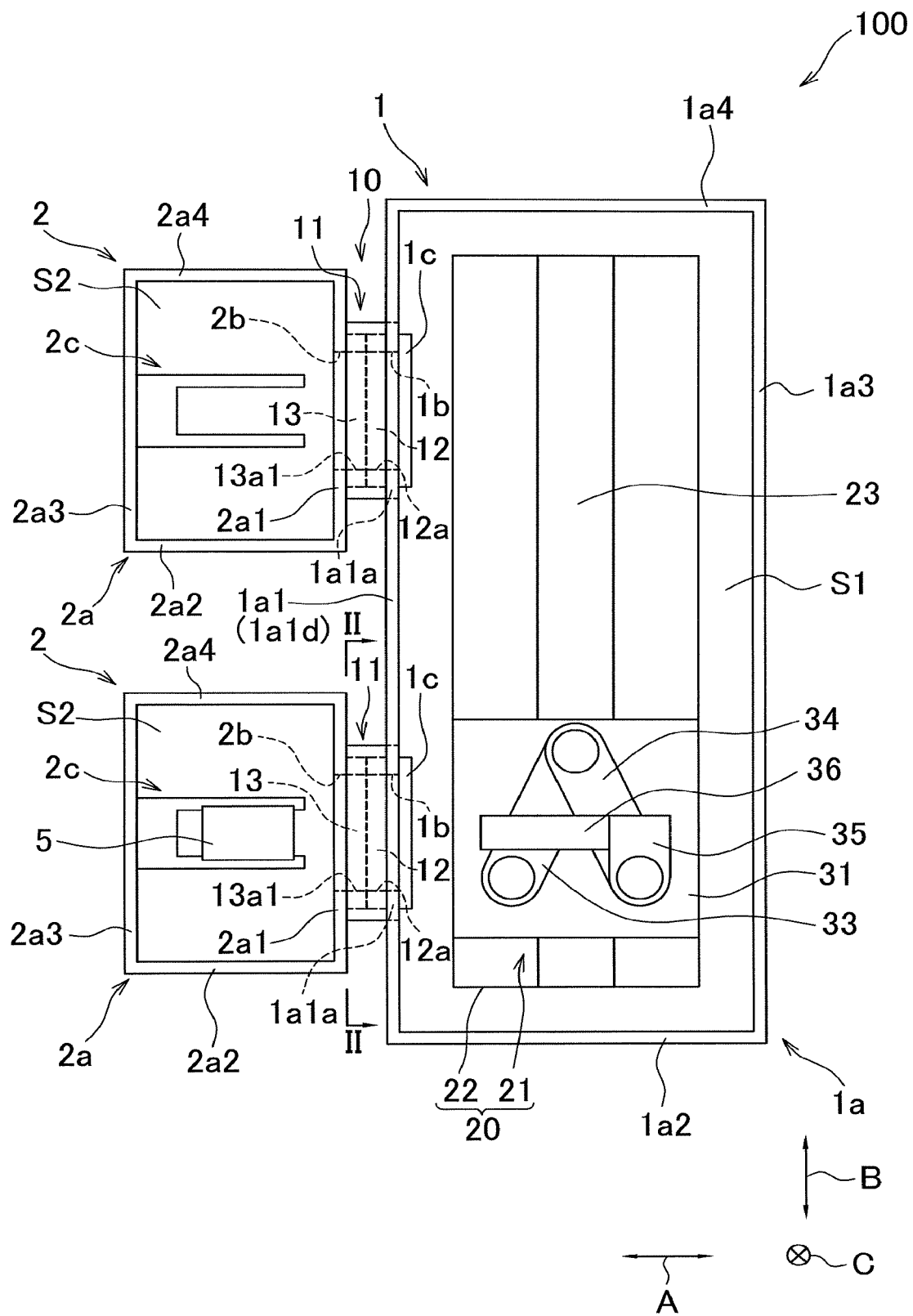
FIG. 1 is a plan view showing the outline of a culture apparatus which employs a connection mechanism of an embodiment of the present invention.

The culture apparatus 100 is an apparatus for culturing cells, in which cells and a culture solution are placed in a culture vessel 5 (e.g., a microplate). As shown in FIG. 1, the culture apparatus 100 includes a conveyor 1 for conveying the culture vessel 5, two processing apparatuses 2, and a connection mechanism 10 for connecting the conveyor 1 to the two processing apparatuses 2. The conveyor 1 includes a housing 1a. The housing 1a includes four side walls 1a1 to 1a4 which define an internal space S1. In the side wall 1a1, two openings 1b are formed to penetrate the same in a first horizontal direction A (thickness direction). These openings 1b are provided to be side by side in a second horizontal direction B which is orthogonal to the first horizontal direction A. On the inner surface of the side wall 1a1, two doors 1c are provided to be able to open and close the opening 1b. When the opening 1b is closed by the doors 1c, the internal space S1 is a sealed space.

Each processing apparatus 2 is detachably connected to the conveyor 1 via each connection part 11 (described later) of the connection mechanism 10. The processing apparatus 2 includes a housing 2a. The housing 2a includes four side walls 2a1 to 2a4 which define an internal space S2. In the side wall 2a1, an opening 2b is formed to penetrate the same in the first horizontal direction A. The opening 2b is provided to be able to face the opening 1b in the first horizontal direction A when the processing apparatus 2 is connected to the conveyor 1. This arrangement allows a SCARA robot 21 (described later) of the conveyor 1 to take the culture vessel 5 in and out of the processing apparatus 2. The internal spaces S1 and S2 of the conveyor 1 and each processing apparatus 2 form a single continuous sealed space after the conveyor 1 is connected to each processing apparatus 2. To put it differently, the connection mechanism 10 connects the conveyor 1 to each processing apparatus 2 in such a way that the two openings 1b of the conveyor 1 communicate with the openings 2b of two processing apparatuses 2.

As shown in FIG. 1, the processing apparatus 2 includes a mounting portion 2c which protrudes from the inner surface of the side wall 2a3 of the housing 2a. The mounting portion 2c is formed by a plate member which is U-shaped in plan view, and supports the both ends in the width direction (i.e., the direction in parallel to the second horizontal direction B) of the culture vessel 5. The processing apparatus 2 may be of any type as long as it has a mounting portion 2c and is used for culturing cells. Furthermore, the mounting portion 2c may be differently structured as long as the culture vessel 5 can be taken in and out by the SCARA robot 21.

As shown in FIG. 1, the conveyor 1 includes a conveyance mechanism 20 which is configured to convey the culture vessel 5. As shown in FIG. 1, the conveyance mechanism 20 includes the SCARA robot 21 and a supporting portion 22 which supports the SCARA robot 21 to be movable in the direction in which the processing apparatuses 2 are lined up (i.e., the second horizontal direction B). The SCARA robot 21 includes a running portion 31, three arms 33 to 35, an elevation portion (not illustrated) for moving up and down the three arms 33 to 35, a supporting plate 36, and a driving portion (not illustrated) configured to drive the running portion 31, the three arms 33 to 35, and the elevation portion. The supporting portion 22 is rectangular parallelepiped in shape and long in the second horizontal direction B. On the top surface of this portion, a rail 23 is formed. The rail 23 is shaped to be long in the second horizontal direction B.

The running portion 31 is provided on the rail 23. The running portion 31 is driven by the driving portion to move on the rail 23 along the second horizontal direction B. In other words, the entire SCARA robot 21 moves along the second horizontal direction B. The elevation portion is provided on the running portion 31 and is connected to the arm 33. The elevation portion is driven by the driving portion so as to move the arm 33 up or down in the up-down direction. In other words, the elevation portion moves the three arms 33 to 35 and the supporting plate 36 up or down in the up-down direction C.

The arm 33 has one end portion which is rotatably connected to the upper surface of the elevation portion. The arm 33 has the other end portion which is rotatably connected to one end portion of the arm 34. The arm 34 has the other end portion which is rotatably connected to one end portion of the arm 35. The other end portion of the arm 35 is fixed to the supporting plate 36. The supporting plate 36 is a plate member which is long and supports the culture vessel 5 from below. These three arms 33 to 35 are rotated along the horizontal rotational direction by the driving portion, so as to move the supporting plate 36 in the direction in parallel to the first horizontal direction A. Such a conveyance mechanism 20 makes it possible to convey the culture vessel 5 from one processing apparatus 2 to another processing apparatus 2 in the sealed space.

As shown in FIG. 1, the connection mechanism 10 includes two connection parts 11. Because these connection parts 11 are identical with each other, the following will describe one connection part 11. As shown in FIG. 2 to FIG. 7, the connection part 11 includes two flanges, i.e., first and second flanges 12 and 13, a movable member 14, an attaching portion 15 by which the first flange 12 is attached to the side wall 1a1 of the housing 1a (conveyor 1), two sealing members 16 and 17, and an attachment (not illustrated) by which the second flange 13 is attached to the side wall 2a1 of the housing 2a (processing apparatus 2). The second flange 13 of the present embodiment is attached to the side wall 2a1 of the housing 2a by the attachment formed of a plurality of screws.

Figure 4:
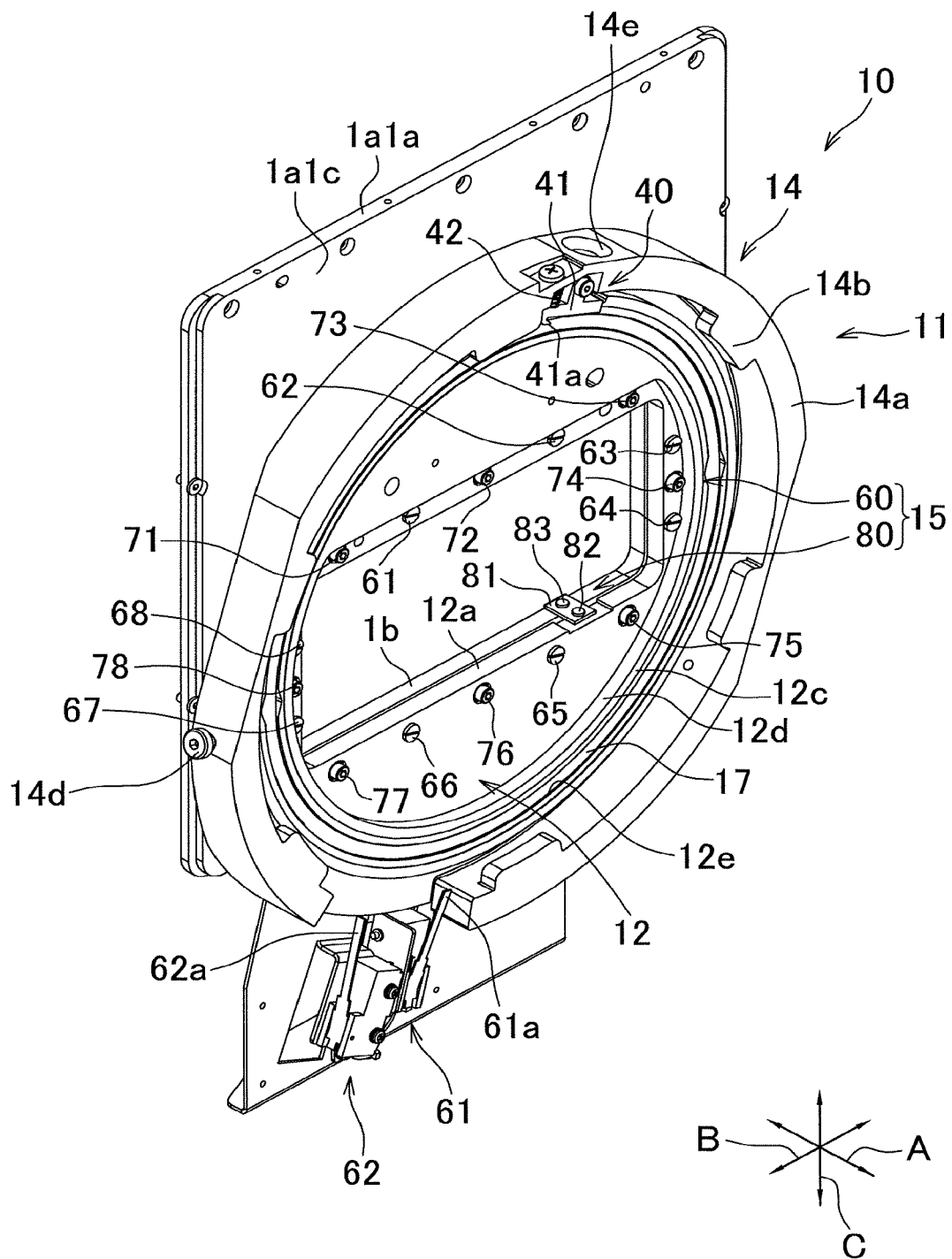
FIG. 4 is a perspective view showing a state in which a second flange of a connection part shown in FIG. 3 has been detached.
Figure 5:
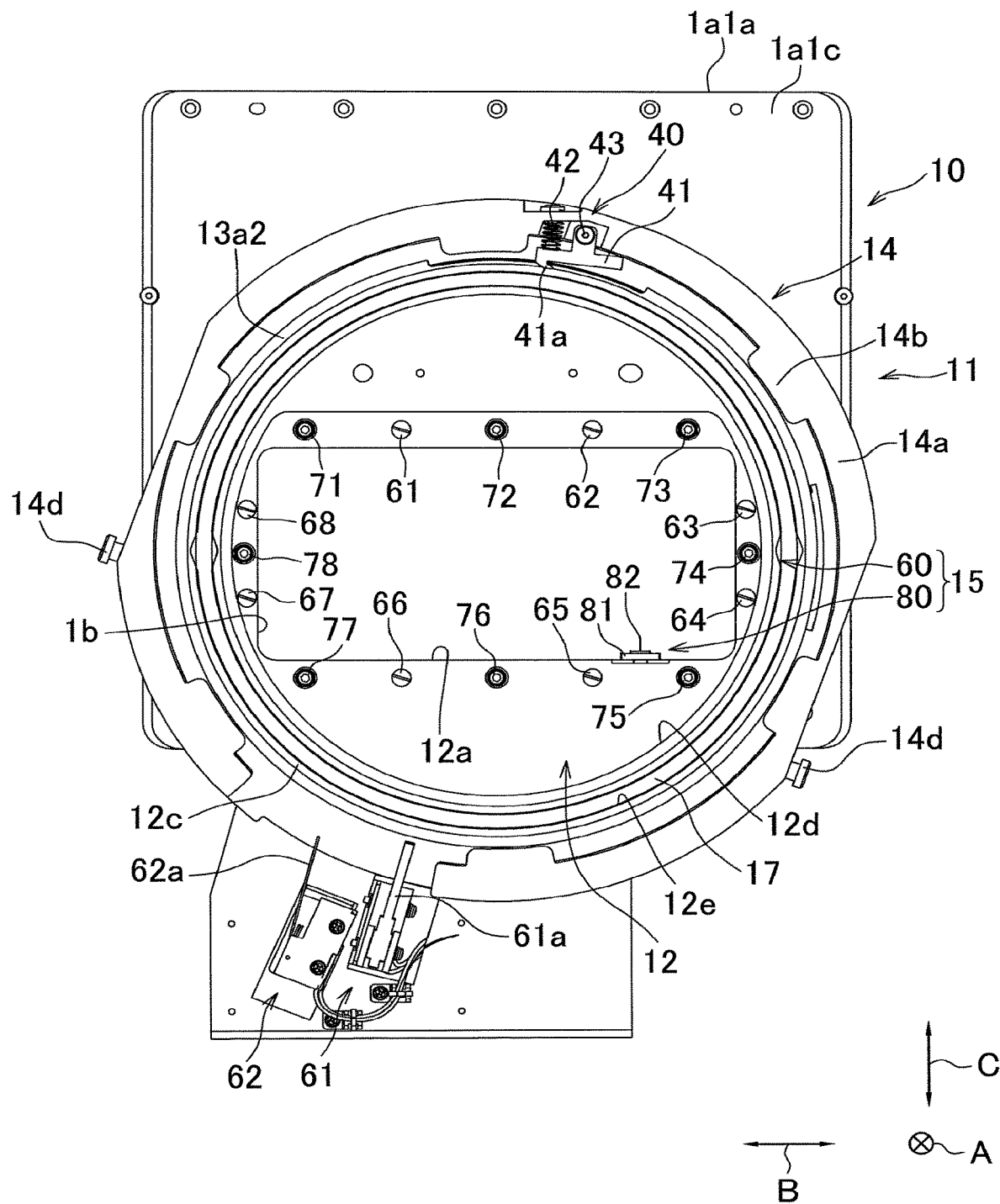
FIG. 5 shows the state in which the second flange of the connection part shown in FIG. 3 has been detached.
Figure 6:
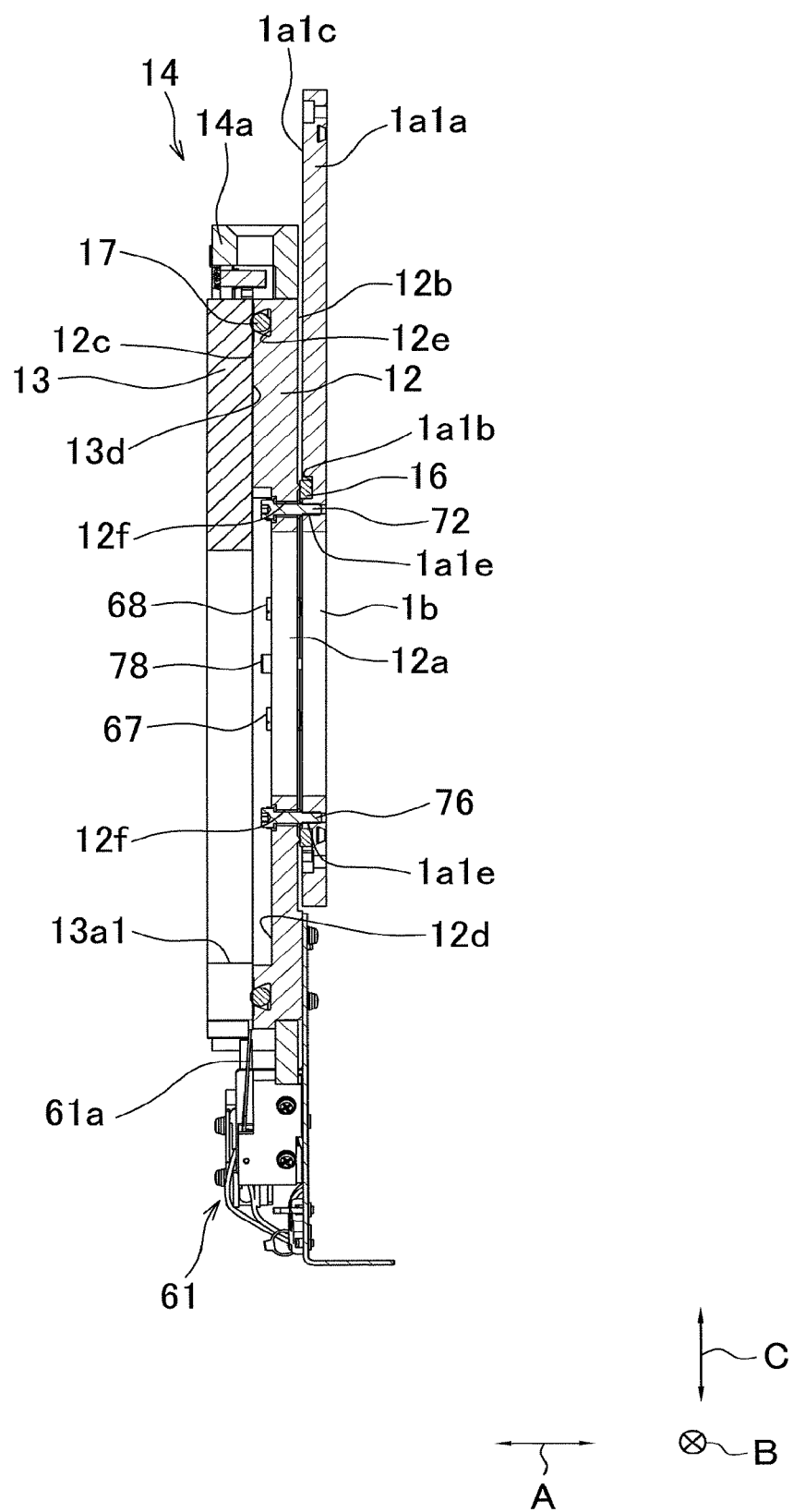
FIG. 6 is a cross section taken along a line VI-VI in FIG. 2.

The first flange 12 is circular and substantially flat in shape, as shown in FIG. 4 to FIG. 7. As shown in FIG. 6, in a surface 12c of the first flange 12, which is opposite to a surface 12b facing the side wall 1a1 (partial wall portion 1a1a) of the first flange 12, a concave portion 12d is formed to be open toward the second flange 13. As shown in FIG. 5 and FIG. 6, at a bottom portion of the concave portion 12d and the center of the first flange 12, a through hole 12a is formed to penetrate the first flange 12 in the thickness direction (first horizontal direction A). As shown in FIG. 5, the through hole 12a is rectangular in plan view and long in the second horizontal direction B. While the opening 1b formed in the side wall 1a1 is arranged to be identical in shape and size with the through hole 12a, the opening 1b may be slightly different in shape and size from the through hole 12a.

Figure 2:
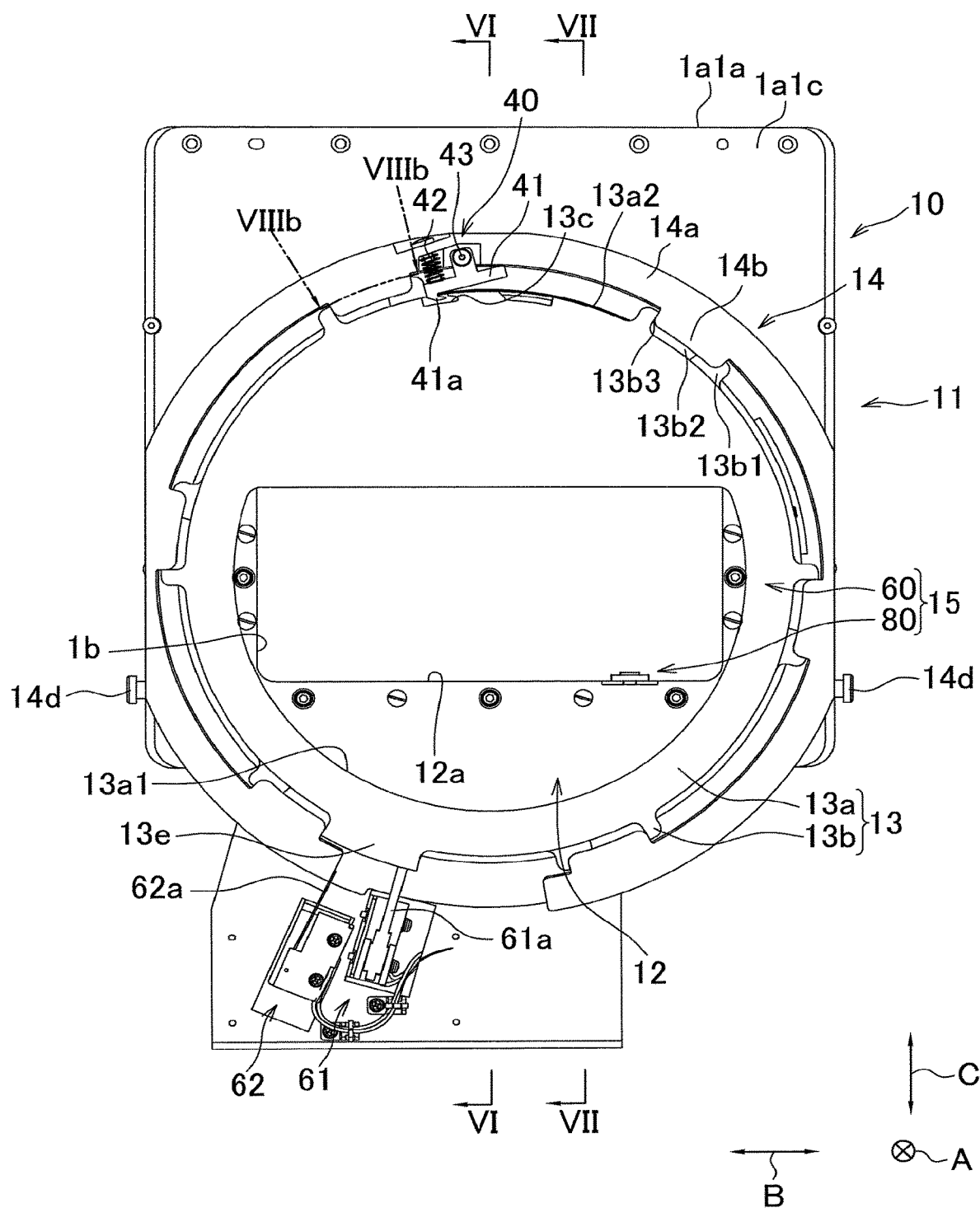
FIG. 2 is a cross section taken along a line II-II in FIG. 1 and shows a state when a movable member is at a locked position.

The first flange 12 is attached by the attaching portion 15 to a partial wall portion 1a1a which is a part of the side wall 1a1, so that the through hole 12a is matched with the opening 1b. As shown in FIG. 2 and FIG. 6, the partial wall portion 1a1a is formed of a substantially square plate member, and is attached to a main body laid (see FIG. 1) of the side wall 1a1 by screws after being accurately positioned to the main body laid. The opening 1b is formed in the partial wall portion 1a1a.

Figure 7:
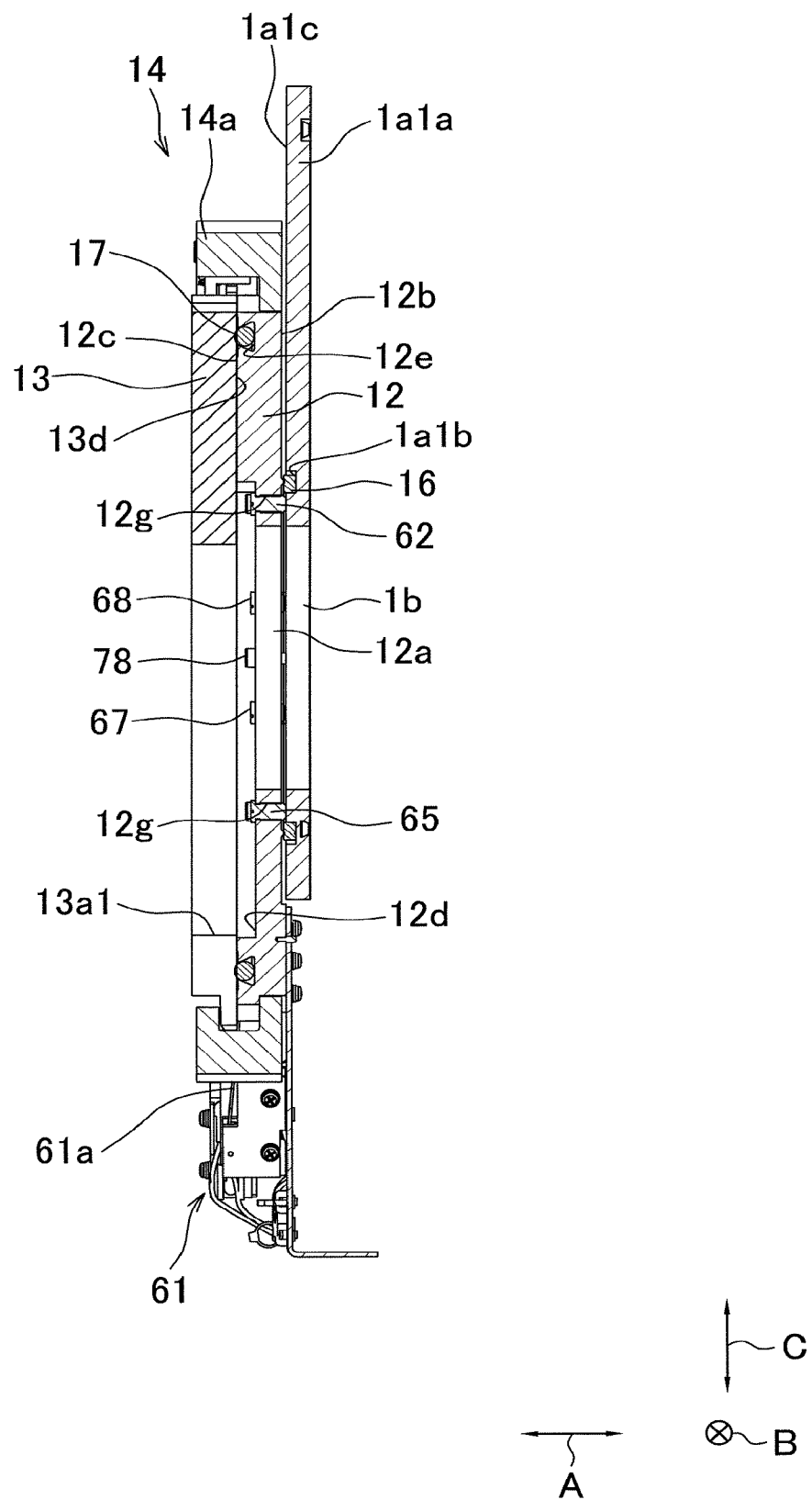
FIG. 7 is a cross section taken along a line VII-VII in FIG. 2.

As shown in FIG. 6 and FIG. 7, the sealing member 16 is provided in an annular concave portion 1a1b formed in the surface 1a1c of the partial wall portion 1a1a facing the first flange 12 so as to seal the gap between the surface 1a1c and the surface 12b of the first flange 12. The concave portion 1a1b is formed to surround the opening 1b. Being similar to the concave portion 1a1b, the sealing member 16 is formed to be annular in shape. The sealing member 16 is made of an elastic material such as rubber. Between the partial wall portion 1a1a and the first flange 12, the sealing member 16 is provided in the concave portion 1a1b to surround the opening 1b and the through hole 12a. The thickness of the sealing member 16 (i.e., the width in the first horizontal direction A) is longer than the depth of the concave portion 1a1b, and hence the sealing member 16 provided in the concave portion 1a1b protrudes to the first flange 12 side as compared to the surface 1a1c. The range of elastic deformation of the sealing member 16 in the present embodiment is from a position where the surface 12b of the first flange 12 makes contact with the sealing member 16 without exerting a pressure onto the sealing member 16 to a position where the surface 12b makes contact with the surface 1a1c of the partial wall portion 1a1a.

As shown in FIG. 6 and FIG. 7, the sealing member 17 is provided in the annular concave portion 12e formed in the surface 12c of the first flange 12 in order to seal the gap between the surface 12c and a surface 13d of the second flange 13. The concave portion 12e is formed to surround the through hole 12a and the concave portion 12d. Being similar to the concave portion 12e, the sealing member 17 is formed to be annular in shape. Being similar to the sealing member 16, the sealing member 17 is made of an elastic material such as rubber. As shown in FIG. 6, between the first and second flanges 12 and 13, the sealing member 17 is provided in the concave portion 12e to surround the through hole 12a and a through hole 13a1 (described later). The thickness of the sealing member 17 (i.e., the width in the first horizontal direction A) is longer than the depth of the concave portion 12e, and hence the sealing member 17 provided in the concave portion 12e protrudes to the second flange 13 side as compared to the surface 12c. With this sealing member 17, airtightness between the first flange 12 and the second flange 13 is effectively maintained.

As shown in FIG. 2, FIG. 3, FIG. 6, and FIG. 7, the second flange 13 includes a flange main body 13a which is circular and flat in shape and six protrusions 13b formed at an outer circumference side face 13a2 of the flange main body 13a. In the flange main body 13a, a through hole 13a1 is formed to penetrate the flange main body 13a in the thickness direction (first horizontal direction A). While the through hole 13a1 of the present embodiment is formed to be larger than the through hole 12a of the first flange 12, the through hole 13a1 may be identical or smaller than the through hole 12a. The through hole 13a1 is formed to face the most of the through hole 12a when the second flange 13 is connected to the first flange 12. While the opening 2b formed in the side wall 2a1 of the housing 2a is formed to be identical in shape and size with the through hole 13a1, the opening 2b may be slightly different in shape and size from the through hole 13a1. The second flange 13 is attached to the side wall 2a1 by the above-described attachment (screws) so that the through hole 13a1 is matched with the opening 2b.

Figure 3:
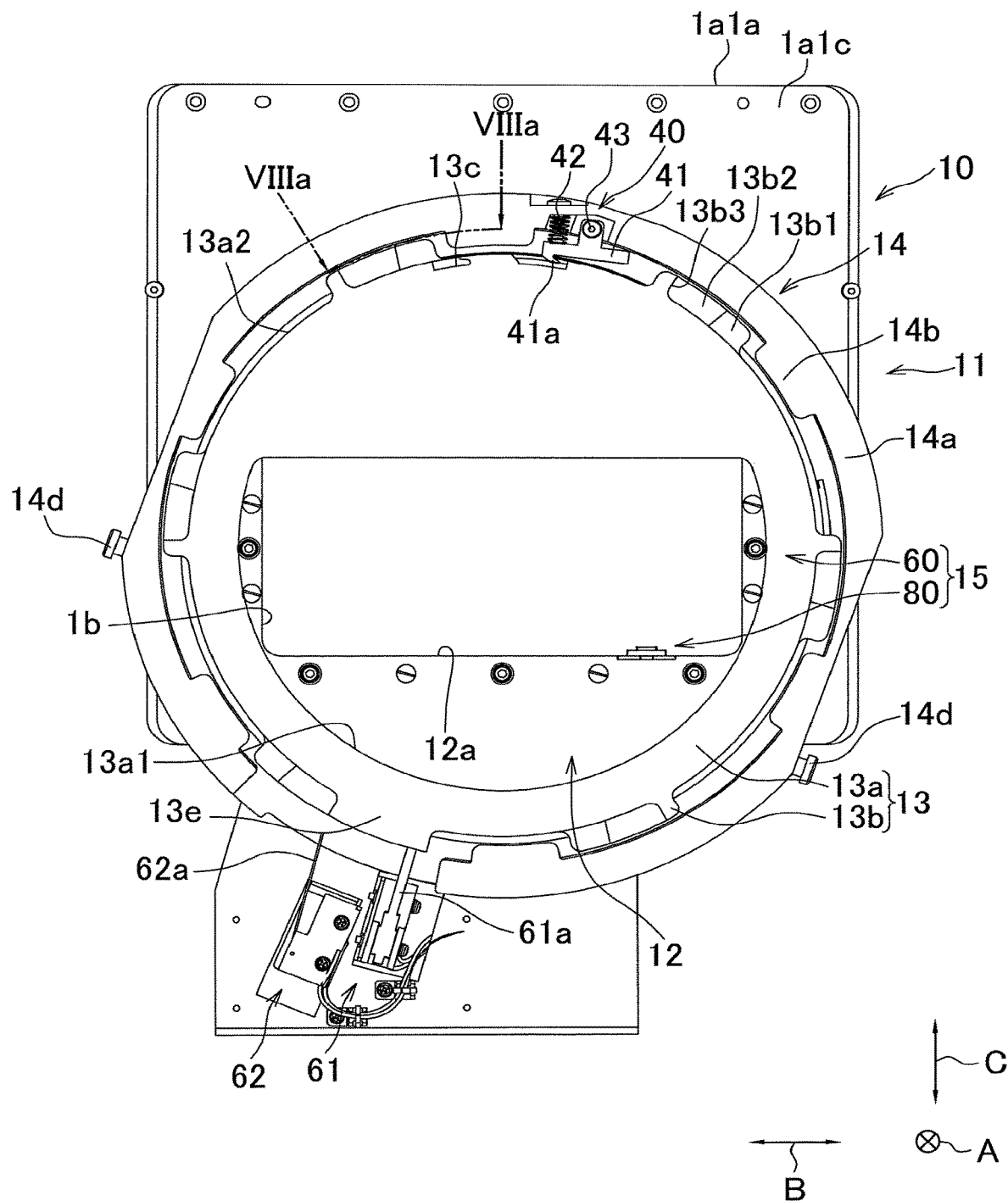
FIG. 3 shows a state when the movable member in FIG. 2 is at an unlocked position.
Figure 8A:
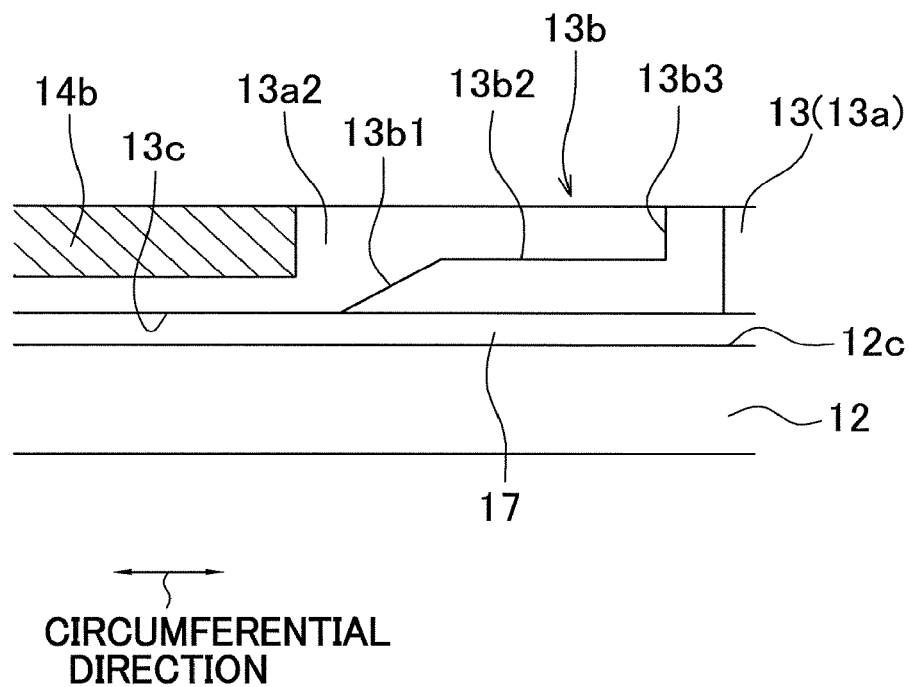
FIG. 8A is a cross section taken along a line VIIIa-VIIIa in FIG. 3.
Figure 8B:
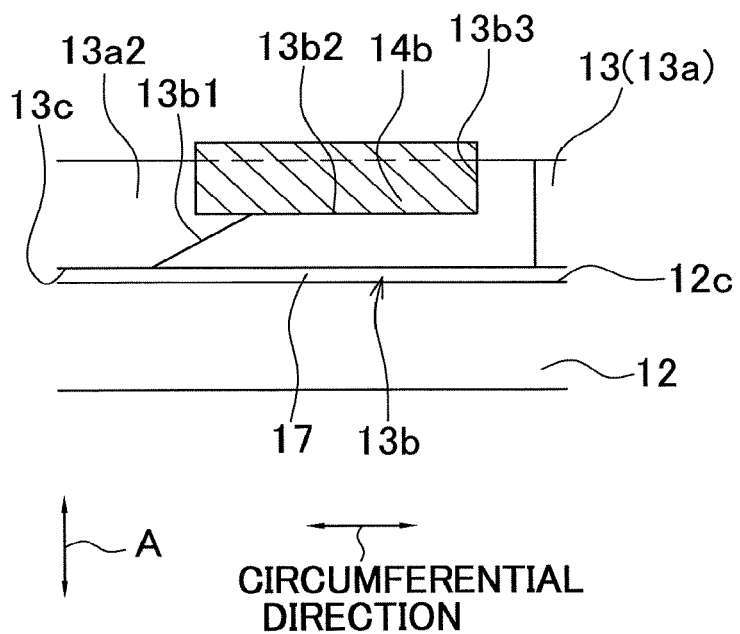
FIG. 8B is a cross section taken along a line VIIIb-VIIIb in FIG. 2.
Figure 9:
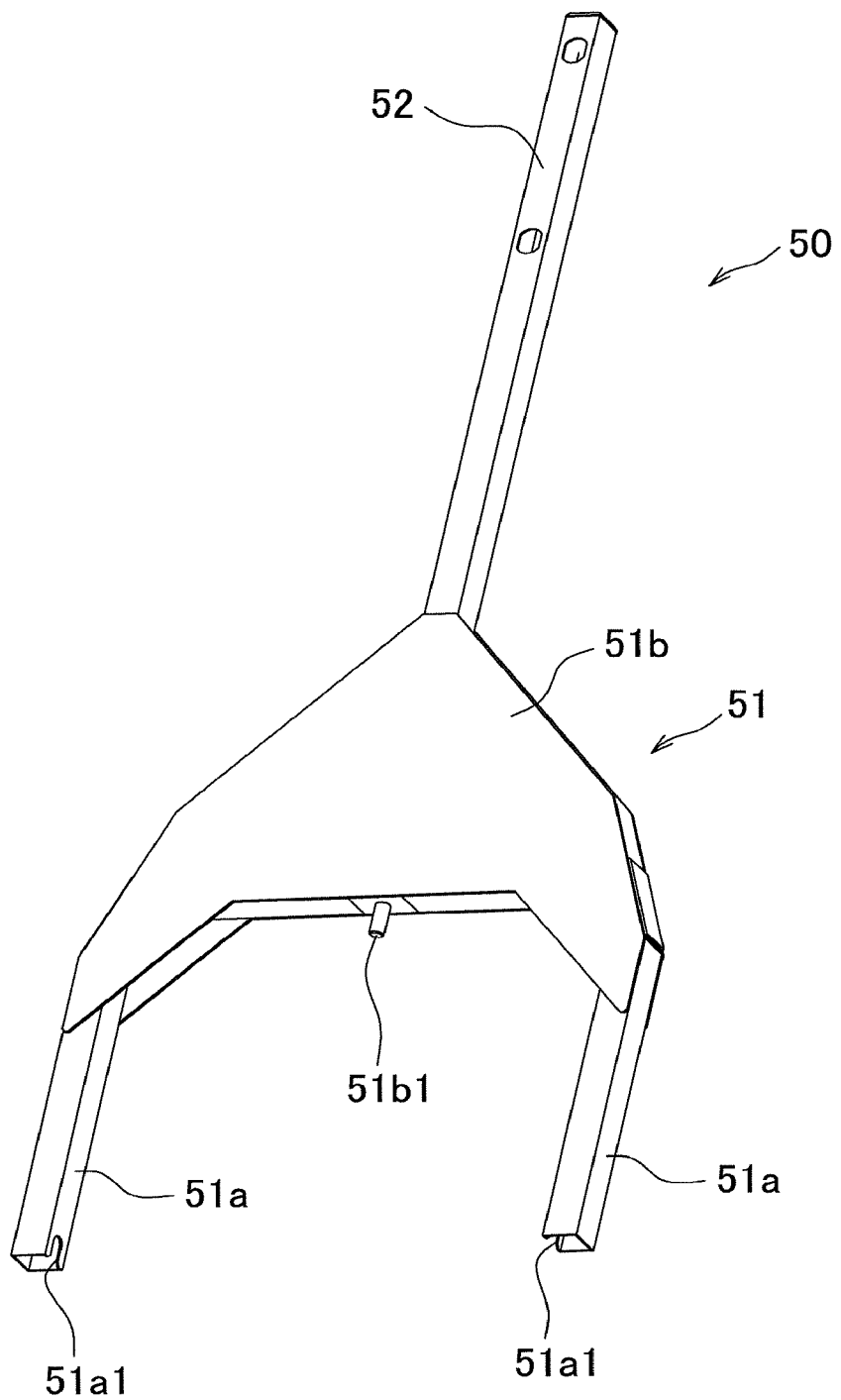
FIG. 9 is a perspective view of a rotational jig.

As shown in FIG. 3, the six protrusions 13b protrude outward along the direction of the diameter of the flange main body 13a, from the outer circumference side face 13a2 of the flange main body 13a. The six protrusions 13b are provided at regular intervals in the circumferential direction along the outer circumference side face 13a2 of the flange main body 13a. As shown in FIG. 8A and FIG. 8B, each protrusion 13b is formed on a surface opposite to the first flange 12 and has a slope surface 13b1, a connection surface 13b2, and a regulating surface 13b3. The slope surface 13b1 is inclined away from the first flange 12 so that the thickness of the protrusion 13b increases from one end (left end in each of FIG. 8A and FIG. 8B) toward the other end (right end in each of FIG. 8A and FIG. 8B) of the protrusion 13b in the circumferential direction. The connection surface 13b2 is a flat surface along the circumferential direction and connects the right end of the slope surface 13b1 to the regulating surface 13b3. The regulating surface 13b3 extends from the other end (right end in each of FIG. 8A and FIG. 8B) of the connection surface 13b2 in the direction away from the first flange 12 (i.e., the first horizontal direction A). The regulating surface 13b3 makes contact with a press portion 14b (described later) of the movable member 14 so as to regulate the rotation of the movable member 14.

As shown in FIG. 2, on the outer circumference side face 13a2 of the flange main body 13a, a hooking portion 13c on which a hook 41a of a later-described rotation regulating mechanism 40 can be hooked is formed. The hooking portion 13c is constituted by a concave portion formed in the outer circumference side face 13a2 of the flange main body 13a. The hooking portion 13c is provided at a position where the hook 41a is able to enter the hooking portion 13c when the movable member 14 is moved to a later-described locked position.

Below the flange main body 13a, a contact portion 13e is formed on the outer circumference side face 13a2. The contact portion 13e also protrudes outward along the direction of the diameter of the flange main body 13a, from the outer circumference side face 13a2 of the flange main body 13a. The contact portion 13e is formed to be integrated with one protrusion 13b below the contact portion 13e. The contact portion 13e is formed to be in contact with a lever 61a of a later-described switch 61 when the surface 13d of the second flange 13, which is opposite to the surface facing the housing 2a, faces the surface 12c of the first flange 12.

As shown in FIG. 2 to FIG. 5, the movable member 14 is C-shaped. As shown in FIG. 4, FIG. 6, and FIG. 7, the movable member 14 is supported by an outer peripheral end portion of the first flange 12 to be movable along the outer peripheral end portion. To be more specific, the movable member 14 is supported by the outer peripheral end portion of the first flange 12 to be rotatable about the center of the first flange 12. The movable member 14 is arranged to be rotatable about the center of the first flange 12, between the locked position shown in FIG. 2 and the unlocked position shown in FIG. 3. The locked position is a position where the connection between the first flange 12 and the second flange 13 is maintained. The unlocked position is a position where the connection between the first flange 12 and the second flange 13 is canceled.

As shown in FIG. 6 and FIG. 7, the movable member 14 has a protruding portion 14a which protrudes along the first horizontal direction A away from the partial wall portion 1a1a (housing 1a) as compared to the surface 12c of the first flange 12. As shown in FIG. 4, on this protruding portion 14a, six press portions 14b are formed to protrude inward from the inner circumferential surface. As shown in FIG. 2, being similar to the six protrusions 13b, the six press portions 14b are provided at regular intervals in the circumferential direction along the inner circumferential surface of the protruding portion 14a. These press portions 14b are arranged to be engaged with the protrusions 13b so as to press the second flange 13 onto the first flange 12, when the movable member 14 is moved counterclockwise from the unlocked position shown in FIG. 3 to the locked position shown in FIG. 2 while the surface 12c of the first flange 12 faces the surface 13d of the second flange 13.

To be more specific, as shown in FIG. 8A, when the movable member 14 is at the unlocked position, the press portions 14b is remote from the protrusion 13b in the circumferential direction but the press portion 14b is positioned to overlap the slope surface 13b1 along the circumferential direction. On this account, as shown in FIG. 8B, when the movable member 14 rotates to the locked position, the right end of the press portion 14b shown in FIGS. 8A and 8B makes contact with the slope surface 13b1, with the result that the second flange 13 is pressed toward the first flange 12. At this stage, because the sealing member 17 is elastically deformed, the second flange 13 and the first flange 12 are maintained to be close to each other. With this arrangement, when the housing 1a is connected to the housing 2a via the connection part 11, the connection is made while the flanges 12 and 13 are closely in contact with each other, as the movable member 14 is rotated. The press portions 14b may be interchanged with the protrusions 13b. In other words, the first and second flanges 12 and 13 are maintained to be close to each other when members equivalent to the press portions 14b are formed on the second flange 13 in place of the protrusions 13b and members which are equivalent to the protrusions 13b but are rotated for 180 degrees are formed on the movable member 14 instead of the press portions 14b.

As shown in FIG. 2, the movable member 14 is provided with the rotation regulating mechanism 40. The rotation regulating mechanism 40 includes a rotational portion 41 supported by the movable member 14 to be rotatable about an axis 43 which is in parallel to the first horizontal direction A and a coil spring 42 biasing the rotational portion 41. The rotational portion 41 has one end at which a hook 41a capable of being engaged with the hooking portion 13c is provided. The coil spring 42 biases the rotational portion 41 so that the hook 41a comes close to the outer circumference side face 13a2 of the flange main body 13. As shown in FIG. 4, in the vicinity of the rotation regulating mechanism 40 of the movable member 14, a through hole 14e is formed to penetrate the second flange 13 in the diameter direction. The through hole 14e is formed at a position facing the other end of the rotational portion 41.

As shown in FIG. 2 to FIG. 5, on the outer circumference side face of the movable member 14, paired protrusions 14d are formed. These paired protrusions 14d are hooked on recessed portions 51a1 of a rotational jig 50 shown in FIG. 9. The rotational jig 50 includes an U-shaped hooking portion 51 and a rod-shaped holding portion 52 connected to the hooking portion 51. The holding portion 52 is formed of a square pipe which linearly extends. The hooking portion 51 includes paired square pipes 51a extending in parallel to the holding portion 52 and a connecting portion 51b connecting the paired square pipes 51a with each other. At a leading end of each square pipe 51a, the recessed portion 51a1 is formed. On the connecting portion 51b, a protrusion 51b1 is formed to protrude in the direction in which the paired square pipes 51a extend. When the rotational jig 50 is attached to the movable member 14, the protrusion 51b1 is inserted into the through hole 14e so that the leading end of the protrusion 51b1 presses the other end of the rotational portion 41 toward the flange main body 13a.

Figure 10:
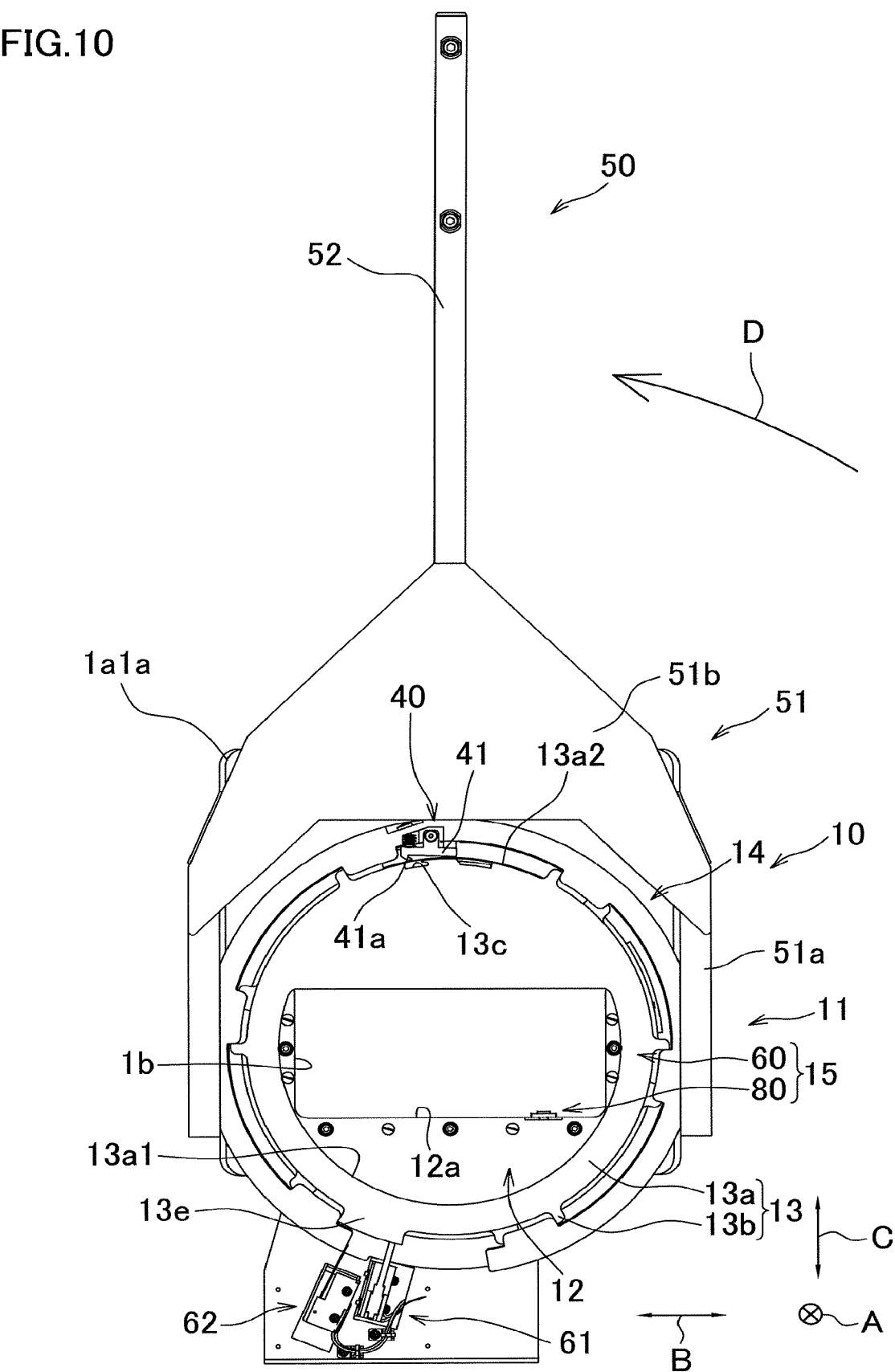
FIG. 10 shows a state in which the movable member of the connection part has been rotated to the locked position by the rotational jig.

As shown in FIG. 10, the rotational jig 50 is attached to the movable member 14 by hooking the recessed portions 51a1 of the rotational jig 50 on the protrusions 14d. At this stage, the rotational portion 41 is rotated by the protrusion 51b1 so that the hook 41a is moved away from the flange main body 13a. As the rotational jig 50 in this state is rotated in the direction indicated by the arrow D in FIG. 10, the movable member 14 moves from the unlocked position to the locked position. Thereafter, the rotational jig 50 is detached from the movable member 14, with the result that the engagement between the protrusion 51b1 and the rotational portion 41 is canceled and the hook 41a is inserted into the hooking portion 13c, as shown in FIG. 2. With this arrangement, even if one tries to rotate the movable member 14 from the locked position to the unlocked position without attaching the rotational jig 50 thereto, the rotation of the movable member 14 is obstructed as the hook 41a is hooked on the hooking portion 13c. After the rotational jig 50 is attached to the movable member 14, the hook 41a can be moved out from the hooking portion 13c. On this account, when the movable member 14 is rotated from the locked position to the unlocked position, the movable member 14 is rotated in the direction opposite to the direction indicated by the arrow D in FIG. 10, after the rotational jig 50 is attached.

As shown in FIG. 2, the connection mechanism 10 includes two switches 61 and 62. The switch 61 includes the lever 61a which is rotatable between a first position and a second position. The first position is a position shown in FIG. 4 and is a position at which the lever 61a is provided when the lever 61a is not in contact with the contact portion 13e of the second flange 13. The second position is a position shown in FIG. 6 and is a position where the lever 61a is positioned due to contact with the contact portion 13e when the second flange 13 is arranged to face the first flange 12. As the lever 61a makes contact with the contact portion 13e of the second flange 13 and moves from the first position to the second position (see FIG. 3 and FIG. 6), the switch 61 outputs a signal indicating that the second flange 13 is arranged to face the first flange 12 to a controlling unit (not illustrated) of the culture apparatus 100. This arrangement makes it possible to detect that the surface 13d of the second flange 13 has been arranged to face the surface 12c of the first flange 12.

The switch 62 includes a lever 62a which is rotatable between a third position and a fourth position. The third position is a position shown in FIG. 3 and is a position at which the lever 62a is provided when the lever 62a is not in contact with the movable member 14. The fourth position is a position shown in FIG. 2 and is a position where the lever 62a is positioned due to contact with the movable member 14 when the movable member 14 is moved to the locked position. As the lever 62a makes contact with the movable member 14 moving to the locked position and moves from the third position to the fourth position (see FIG. 2), the switch 62 outputs a signal indicating that the movable member 14 is at the locked position to the controlling unit of the culture apparatus 100. This makes it possible to detect whether the movable member 14 is at the locked position.

As shown in FIG. 5, the attaching portion 15 includes a vertical adjuster 60 which adjusts the surface 12c of the first flange 12 to be vertical and a rotation adjuster 80 which rotates the first flange 12 about a horizontal axis H (see FIGS. 11A and 11B) passing the center of the through hole 12a of the first flange 12 and extending in the first horizontal direction A to adjust the position of attachment to the side wall 1a1. The vertical adjuster 60 includes eight regulating screws 61 to 68 and eight adjusting screws 71 to 78. The eight regulating screws 61 to 68 and the eight adjusting screws 71 to 78 are alternately provided around the through hole 12a, and are separated from one another.

Because the adjusting screws 71 to 78 are structurally identical with one another, the following will describe the adjusting screws 72 and 76 with reference to FIG. 6. As shown in FIG. 6, the adjusting screws 72 and 76 are inserted into through holes 12f formed in the first flange 12, and leading ends of these screws are attached to screw holes 1a1e formed in the partial wall portion 1a1a. The adjusting screws 71 to 78 are provided for adjusting the separation distance between the first flange 12 and the partial wall portion 1a1a and for attaching the first flange 12 to the partial wall portion 1a1a.

Because the regulating screws 61 to 68 are structurally identical with one another, the following will describe the regulating screws 62 and 65 with reference to FIG. 7. As shown in FIG. 7, the regulating screws 62 and 65 are attached to screw holes 12g formed in the first flange 12 so that leading ends of these screws protrude from the surface 12b of the first flange 12 and are able to contact with the partial wall portion 1a1a. In the present embodiment, in the first horizontal direction A, the maximum protruding length of each of the regulating screws 61 to 68 from the surface 12b of the first flange 12 when the regulating screws 61 to 68 are maximally screwed into the first flange 12 is arranged to be equal to or shorter than the protruding length of the sealing member 16 from the surface 1a1c of the partial wall portion 1a1a when the sealing member 16 is not pressed by the surface 12b of the first flange 12. In other words, within the range of elastic deformation of the sealing member 16, the regulating screws 61 to 68 are allowed to regulate the upper limit of the separation distance between the first flange 12 and the partial wall portion 1a1a. In summary, the regulating screws 61 to 68 are required to regulate the separation distance between the first flange 12 and the partial wall portion 1a1a to allow the sealing member 16 to certainly seal the gap between the first flange 12 and the partial wall portion 1a1a.

As shown in FIG. 4, the rotation adjuster 80 includes a plate 81, an adjusting screw 82, and a fixing screw 83. The plate 81 is rectangular in plan view and long in the first horizontal direction A. In the plate 81, through holes (not illustrated) are formed at a position facing the inner circumferential surface of the opening 1b of the partial wall portion 1a1a (i.e., a lower long side 1b1 in FIGS. 11A and 11B) and a position facing the inner circumferential surface of the through hole 12a of the first flange 12 (i.e., a lower long side 12a1 in FIGS. 11A and 11B). These through holes are lined up in the first horizontal direction A. The fixing screw 83 is inserted into the through hole (facing the inner circumferential surface of the opening 1b) of the plate 81 and is attached to a screw hole (not illustrated) formed in the inner circumferential surface of the opening 1b (i.e., the lower long side 1b1). With this arrangement, the plate 81 is fixed to the inner circumferential surface of the opening 1b. The adjusting screw 82 is inserted into the through hole (facing the inner circumferential surface of the through hole 12a) of the plate 81 and is attached to a screw hole (not illustrated) formed in the inner circumferential surface of the through hole 12a (i.e., the lower long side 12a1). The adjusting screw 82 is provided to adjust the attaching position of the first flange 12 about the horizontal axis H by changing the separation distance between the plate 81 and the inner circumferential surface of the through hole 12a, as the adjusting screw 82 is screwed into the screw hole.

The following will describe adjustment of the attaching position of the first flange 12 attached to the housing 1a (side wall 1a1). Before the adjustment of the attaching position of the first flange 12 attached to the housing 1a, the housing 1a (conveyor 1) in which the first flange 12 is attached to the side wall 1a1 (partial wall portion 1a1a) by the attaching portion 15 is installed. At this stage, the installation state is adjusted by an operation of an adjuster (not illustrated) of the housing 1a or the like. Furthermore, the installation state of the housing 1a is adjusted so that the moving direction of the SCARA robot 21 is identical with the second horizontal direction.

After the adjustment of the installation state of the housing 1a, the attaching position of the first flange 12 attached to the housing 1a is adjusted. Two level gauges (not illustrated) are attached at positions above the center of the first flange 12. The first level gauge is attached to be vertical with respect to the surface 12c of the first flange 12. This makes it possible to determine whether the surface 12c of the first flange 12 is vertical. The second level gauge is attached to be in parallel to the long side 12a1 of the through hole 12a of the first flange (i.e., the long side extending in the second horizontal direction B in FIGS. 11A and 11B). This makes it possible to determine the state of the attaching position of the first flange 12 about the horizontal axis H (i.e., whether the long side 12a1 is horizontal or not). At this stage, the rotation adjuster 80 has not been attached yet.

Figure 11A:
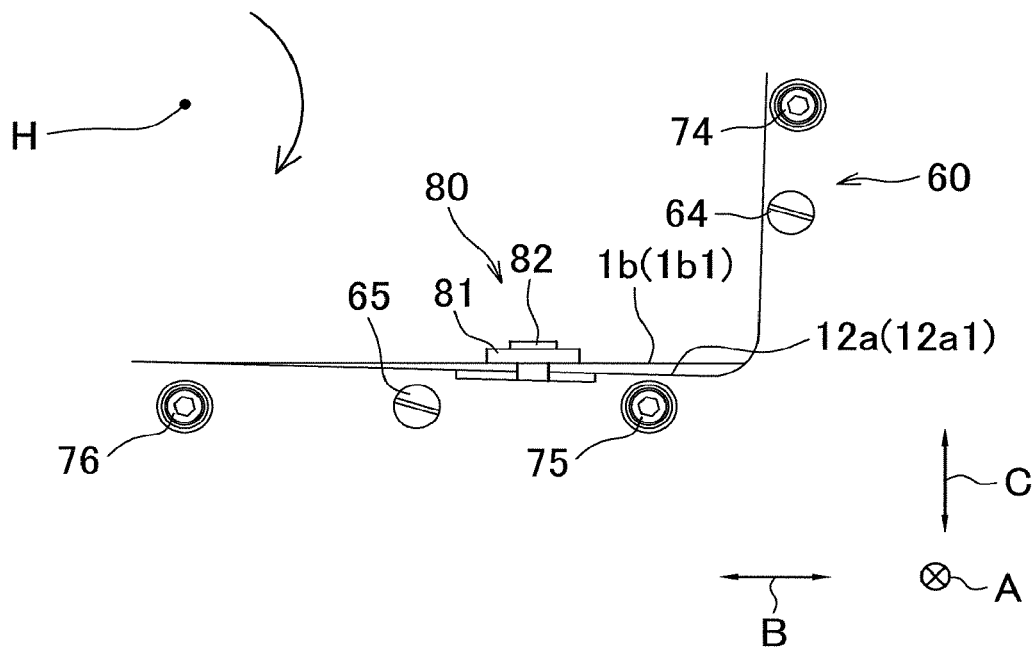
FIG. 11A shows a state of position adjustment about the horizontal axis of a flange.

Subsequently, the adjusting screws 71 to 78 are loosened and the first flange 12 is slightly tilted clockwise as shown in FIG. 11A. As a result, the long side 1b1 below the opening 1b is slightly deviated from the long side 12a1 below the through hole 12a. Thereafter, the plate 81 of the rotation adjuster 80 is attached to the opening 1b by the fixing screw 83. In so doing, the fixing screw 83 is maximally screwed. Thereafter, the adjusting screw 82 is inserted into a through hole of the plate 81 and lightly screwed into a screw hole formed in the inner circumferential surface of the through hole 12a.

Subsequently, the regulating screws 61 to 68 are maximally screwed. At this stage, if the leading ends of the regulating screws 61 to 68 hit the surface 1a1c of the partial wall portion 1a1a and cannot be screwed any more, the adjusting screws 71 to 78 are further loosened to separate the surface 12b of the first flange 12 from the surface 1a1c of the partial wall portion 1a1a. After the regulating screws 61 to 68 are maximally screwed, the adjusting screws 71 to 78 are screwed to cause the surface 12b of the first flange 12 and the surface 1a1c of the partial wall portion 1a1a to come close to each other. At this stage, the adjusting screws 71 to 78 are screwed until the leading ends of the regulating screws 61 to 68 lightly hit the surface 1a1c of the partial wall portion 1a1a. This is the end of preparation of adjustment of the attaching position of the first flange 12 with respect to the side wall 1a1.

Figure 11B:
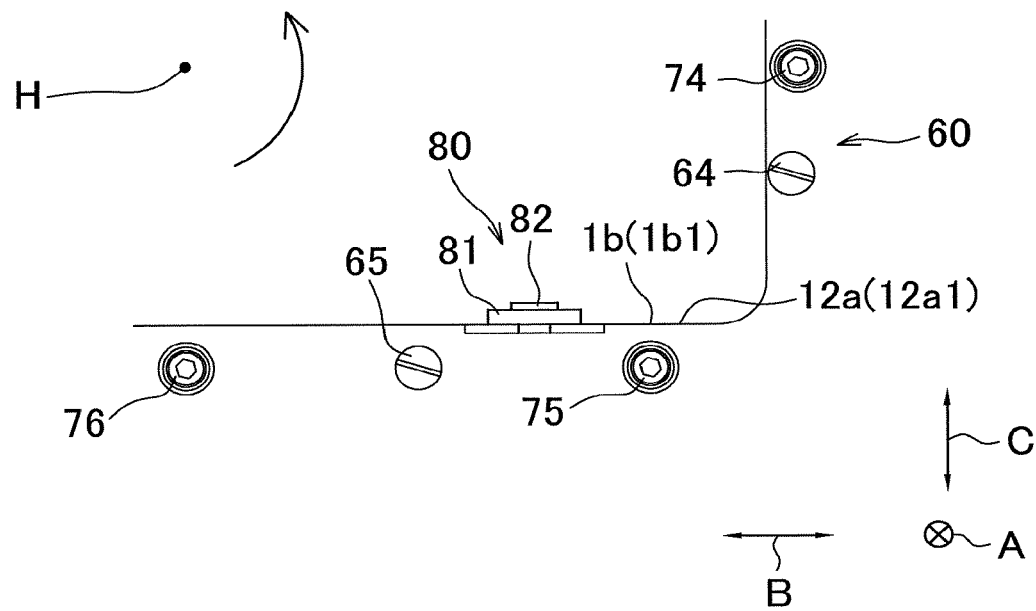
FIG. 11B shows a state of position adjustment about the horizontal axis of a flange.

After this preparation, to begin with, position adjustment of the first flange 12 about the horizontal axis H is carried out. This is because, even if the installation state of the housing 1a is adjusted, the positions of the connection parts 11 may be different from one another about the horizontal axis H of the first flange 12. First, the adjusting screws 71 to 78 are loosened by about a half-rotation. Thereafter, the adjusting screw 82 is screwed. As a result, the first flange 12 rotates counterclockwise about the horizontal axis H, with the result that the long side 12a1 of the through hole 12a moves upward. Then the screwing of the adjusting screw 82 is stopped when the bubble of the second level gauge is substantially at the center in the longitudinal direction of the second level gauge. When the bubble is at the center of the second level gauge, it is indicated that the long side 12a1 of the through hole 12a is horizontal. As a result, as shown in FIG. 11B, the long side 12a1 of the through hole 12a is matched with the long side 1b1 of the opening 1b. Thereafter, the adjusting screws 71 to 78 are screwed until the leading ends of the regulating screws 61 to 68 lightly hit the surface 1a1c of the partial wall portion 1a1a. This is the end of the position adjustment of the first flange 12 about the horizontal axis H.

Figure 12A:
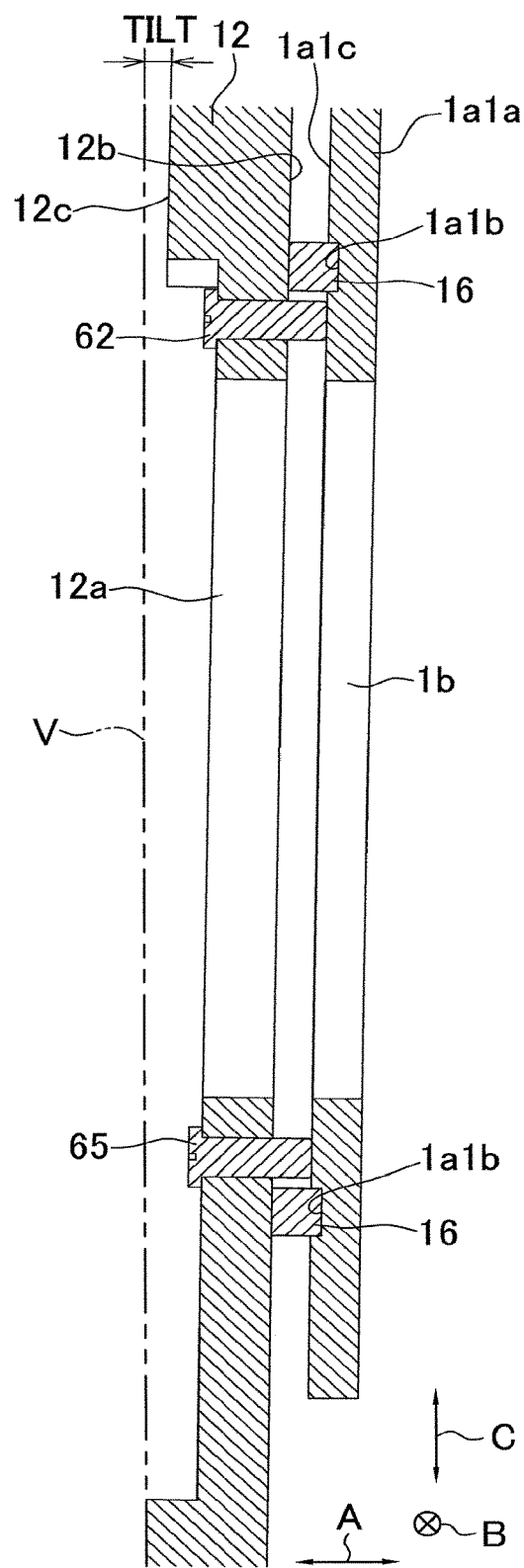
FIG. 12A shows a state of position adjustment when the flange is arranged to be vertical.
Figure 12B:
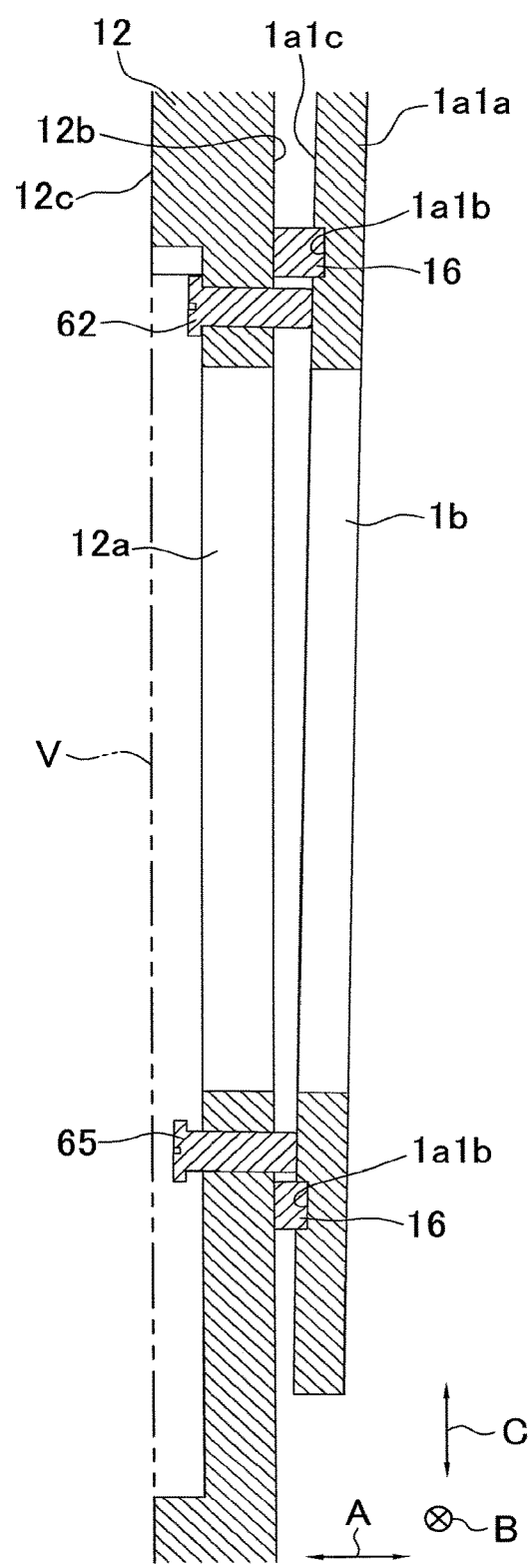
FIG. 12B shows a state of position adjustment when the flange is arranged to be vertical.

Subsequently, position adjustment is carried out to arrange the surface 12c of the first flange 12 to be vertical. This is because, even if the installation state of the housing 1a is adjusted, the partial wall portion 1a1a may be tilted together with the first flange 12 with respect to the vertical line V, as shown in FIG. 12A. In such a case, the state of tilt of the first flange 12 is checked based on the position of the bubble of the first level gauge. As shown in FIG. 12A, when the first flange 12 is tilted so that the upper part of the first flange 12 is farther from the vertical line V than the lower part is and the bubble is on the side far from the first flange 12 as compared to the center of the first level gauge, six regulating screws 63 to 68 are adjusted among the eight regulating screws 61 to 68. To be more specific, each of the six regulating screws 63 to 68 is loosened by one rotation to cause the leading ends of the regulating screws 63 to 68 to be slightly separated from the surface 1a1c of the partial wall portion 1a1a. Thereafter, the adjusting screws 75 and 77 are gradually and evenly screwed to cause the lower part of the first flange 12 to come close to the partial wall portion 1a1a. The screwing of the adjusting screws 75 and 77 is stopped when the bubble of the first level gauge is substantially at the center in the longitudinal direction of the first level gauge. When the bubble is at the center of the first level gauge, it is indicated that the surface 12c of the first flange 12 is vertical. As a result, the surface 12c of the first flange 12 is substantially in parallel to the vertical line V as shown in FIG. 12B. When the bubble of the first level gauge does not reach the center after each of the loosening of the six regulating screws 63 to 68 and the gradual and even screwing of the adjusting screws 75 and 77 is performed once, these operations are alternately repeated.

Meanwhile, when the bubble is on the side close to the first flange 12 as compared to the center of the first level gauge, six regulating screws 61 to 64, 67, and 68 are adjusted among the eight regulating screws 61 to 68. To be more specific, each of the six regulating screws 61 to 64, 67, and 68 is loosened by one rotation to cause the leading ends of the regulating screws 61 to 64, 67, and 68 to be slightly separated from the surface 1a1c of the partial wall portion 1a1a. Thereafter, the adjusting screws 71 and 73 are gradually and evenly screwed to cause the upper part of the first flange 12 to come close to the partial wall portion 1a1a. The screwing of the adjusting screws 71 and 73 is stopped when the bubble of the first level gauge is substantially at the center in the longitudinal direction of the first level gauge. As a result, the surface 12c of the first flange 12 is substantially in parallel to the vertical line. When the bubble of the first level gauge does not reach the center after each of the loosening of the six regulating screws 61 to 64, 67, and 68 and the gradual and even screwing of the adjusting screws 71 and 73 is performed once, these operations are alternately repeated.

After the surface 12c of the first flange 12 is arranged to be vertical, the loosened six regulating screws 63 to 68 (or 61 to 64, 67, and 68) are screwed so that the leading ends of these screws lightly hit the surface 1a1c of the partial wall portion 1a1a. Thereafter, the adjusting screws are evenly screwed in such a way that the adjusting screws 71, 75, 73, 77, 72, 76, 78, and 74 are screwed in this order each at least three times. Then the two level gauges are detached. This is the end of adjustment of the attaching position of the first flange 12 with respect to the housing 1a (side wall 1a1). As a result of performing such adjustment of the attaching position of the first flange 12 with respect to the housing 1a (side wall 1a1) for each of the connection parts 11, a difference between two first flanges 12 attached to the housing 1a is decreased.

In the embodiment above, because the attaching portion 15 includes the vertical adjuster 60, it is possible to adjust the surface 12c of the first flange 12 to be vertical in each connection part 11 when the surface 12c of the first flange 12 is not vertical when the housing 1a is installed. Furthermore, because the attaching portion 15 includes the rotation adjuster 80, a positional deviation of the flange about the horizontal axis H, which occurs when the housing 1a is installed, is adjustable at each connection part 11. Because the attaching position of the first flange 12 with respect to the housing 1a is individually adjustable in this way, a difference in the attaching position of the first flange 12 between two connection parts 11 is decreased. Furthermore, because the attaching portion 15 includes both the vertical adjuster 60 and the rotation adjuster 80, the attaching position of the first flange 12 attached to the housing 1a is effectively adjustable.

The connection part 11 includes the sealing member 16 and the vertical adjuster 60 includes the eight regulating screws 61 to 68 and the eight adjusting screws 71 to 78. This arrangement makes it possible to adjust the attaching position of the first flange 12 attached to the housing 1a in such a way that the surface 12c of the first flange 12 is vertical while the airtightness between the first flange 12 and the side wall 1a1 is maintained.

Because the rotation adjuster 80 includes the plate 81 and the adjusting screw 82, it is possible to adjust the attaching position of the first flange 12 with respect to the housing 1a about the horizontal axis H.

While the attaching portion 15 of the embodiment above includes both the vertical adjuster 60 and the rotation adjuster 80, the attaching portion 15 may include only one of them. When the attaching portion 15 includes the vertical adjuster 60, it is possible to adjust the surface 12c of the first flange 12 to be vertical in each connection part 11 when the surface 12c of the first flange 12 is not vertical when the housing 1a is installed. When the attaching portion 15 includes the rotation adjuster 80, a positional deviation of the flange about the horizontal axis H, which occurs when the housing 1a is installed, is adjustable at each connection part 11. Because the attaching position of the first flange 12 with respect to the housing 1a is individually adjustable in this way, a difference in the attaching position of the first flange 12 between two connection parts 11 is decreased in the same manner as above. When the attaching portion includes only the rotation adjuster 80, a means for attaching the first flange 12 to the side wall 1a1, e.g., adjusting screws 71 to 78, is preferably included.

The vertical adjuster may be a vertical adjuster 260 shown in FIG. 13. The vertical adjuster 260 includes a plurality of rod members 261 penetrating the first flange 12 and the partial wall portion 1a1a, a plurality of coil springs 262 attached to the rod members 261, and a plurality of wedge members 263. At the ends of each rod member 261, retainers 261a and 261b are formed to prevent the rod member 261 from dropping off from the first flange 12 and the partial wall portion 1a1a. The coil springs 262 are provided between the partial wall portion 1a1a and the retainers 261b to bias the partial wall portion 1a1a toward the first flange 12. The wedge members 263 are provided between the first flange 12 and the partial wall portion 1a1a to be spaced apart from each other in the up-down direction. When the wedge members 263 are maximally pushed inward along the diameter of the first flange 12, the gap between the first flange 12 and the partial wall portion 1a1a is sealed by the sealing member 16. With this vertical adjuster 260, when the surface 12c of the first flange 12 is not vertical, a predetermined wedge member 263 is moved outward along the direction of the diameter. As a result, the first flange 12 becomes partially close to the partial wall portion 1a1a and hence the surface 12c of the first flange 12 becomes adjustable to be vertical. Effects similar to the above are attained by this vertical adjuster 260. Also in this case, when the attaching portion includes only the vertical adjuster 260, a means for attaching the first flange 12 to the side wall 1a1, e.g., adjusting screws 71 to 78, is preferably included.

Figure 14:
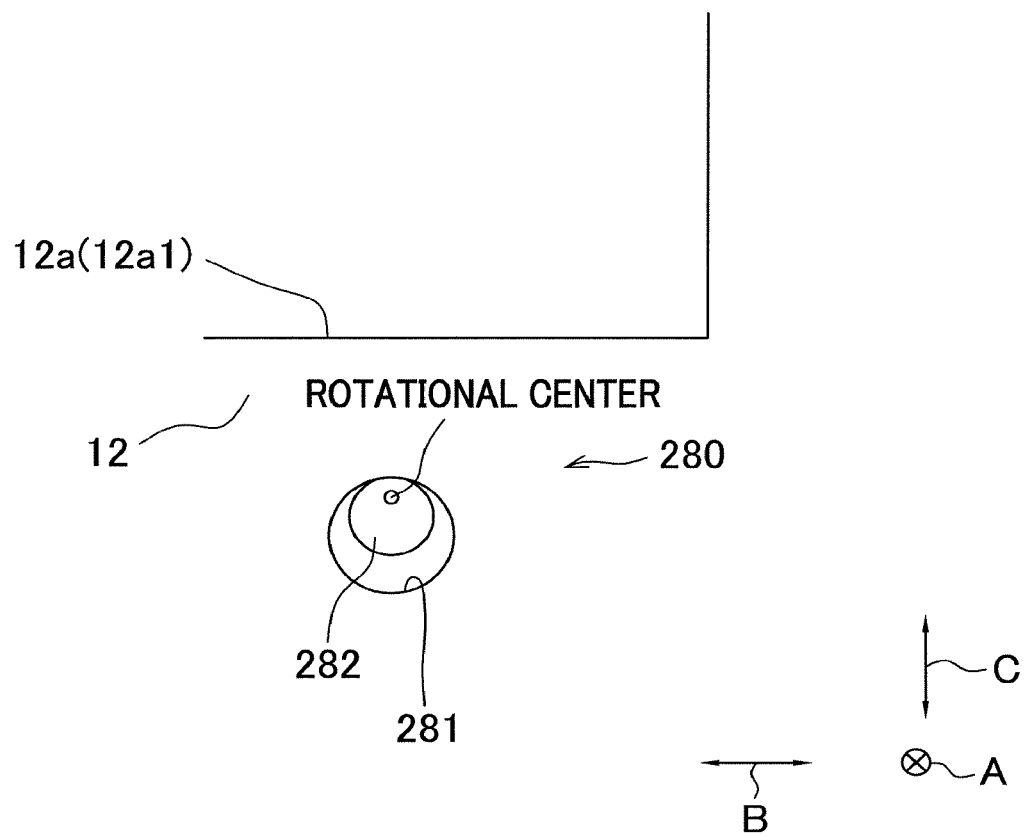
FIG. 14 shows a modification of a rotation adjuster.

The rotation adjuster may be a rotation adjuster 280 shown in FIG. 14. The rotation adjuster 280 may be formed of a circular through hole 281 penetrating the first flange 12 and a disc cam 282 rotatably supported by the partial wall portion 1a1a. The disc cam 282 is provided in the through hole 281. The rotational center of the disc cam 282 is deviated upward from the center of the disc cam 282. With this rotation adjuster 280, as the disc cam 282 is rotated from the position shown in FIG. 14, the first flange 12 rotates about the horizontal axis H and hence the long side 12a1 of the through hole 12a moves upward. The long side 12a1 of the through hole 12a is therefore matched with the long side 1b1 of the opening 1b in the same manner as in the embodiment above, with the result that position adjustment of the first flange 12 about the horizontal axis H is possible.

A preferred embodiment of the present invention has been described. It should be noted that the present invention is not limited to the above-described embodiment, and various changes, substitutions, and alterations can be made herein without departing from the spirit and scope of the invention as defined by the appended claims. While the connection mechanism 10 of the embodiment above is employed in the culture apparatus 100, the application target of the connection mechanism 10 is not limited to the culture apparatus 100. The connection mechanism 10 may be employed in any application targets on condition that a first housing having at least one side wall defining an internal space and a plurality of openings formed in the side wall is connected to a second housing having at least one side wall defining an internal space and a plurality of openings formed in the side wall in such a way that the openings of these housings communicate with one another at a connection part.

In the housings 1a and 2a, the internal space may be defined by a single annular sidewall. Furthermore, the housings 1a and 2a may have two, three, five, or more side walls. While the connection part 11 of the embodiment above includes the second flange 13 which is to be attached to the housing 2a, the connection part 11 may not include the second flange 13. In such a case, the movable member 14 may not be provided, either, and the first flange 12 is directly attached to the side wall 2a1 of the housing 2a. Effects similar to the above are attained in this case, on condition that the connection part 11 includes at least one of the vertical adjuster 60 or the rotation adjuster 80. Furthermore, the first flange 12 may not be circular in shape. Furthermore, the attaching portion by which the second flange 13 of the connection part 11 is attached to the side wall 2a1 of the housing 2a may include at least one of the vertical adjuster 60 or the rotation adjuster 80, which have been described above. This further improves the reliability of the connection between the first and second flanges 12 and 13 of the connection part 11. Furthermore, the housing 1a may have three or more openings 1b. In such a case, the above-described connection mechanism 10 may have three or more connection parts 11 to correspond to the number of the openings 1b.

While the vertical adjuster 60 have eight regulating screws 61 to 68, the number of the regulating screws may be two or more, seven or less, or nine or more. While the vertical adjuster 60 have eight adjusting screws 71 to 78, the number of the adjusting screws may be between two to seven, or nine or more.

While the second flange 13 has six protrusions 13b, the number of the protrusions 13b may be between two to five, or seven or more. While the movable member 14 has six press portions 14b, the number of the press portions 14b may be between two to five, or seven or more, to correspond to the number of the protrusions 13b.

The sealing member 16 may not be provided in the concave portion 1a1b but be attached to the surface 1a1c or the surface 12b by means of an adhesive or the like. In such a case, the regulating screws 61 to 68 are arranged to set the upper limit of the separation distance between the first flange 12 and the partial wall portion 1a1a to be equal to or shorter than the thickness of the sealing member 16 in the first horizontal direction A and allow the sealing member 16 to be elastically deformed (i.e., allow the surface 12b to be movable while being in contact with the sealing member 16).

Reference Signs List 1a housing (first housing)
1a1 to 1a4 side wall (first side wall)
1a1a partial wall portion
1b opening (first opening)
2a housing (second housing)
2a1 to 2a4 side wall (second side wall)
2b opening (second opening)
10 connection mechanism
11 connection part
12 first flange
12a through hole (first through hole)
12b surface
12c surface
13 second flange
13a1 through hole (second through hole)
13b protrusion
14 movable member
14a protruding portion
14b press portion
15 attaching portion
16 sealing member
17 sealing member
60 vertical adjuster (first adjuster)
61 to 68 regulating screw (first screw)
71 to 78 adjusting screw (second screw)
80 rotation adjuster (second adjuster)
81 plate
82 adjusting screw
H horizontal axis
S1 internal space
S2 internal space

The invention claimed is:

1. A connection mechanism comprising a plurality of connection parts which connect a first housing including at least one first side wall defining an internal space and a plurality of first openings formed in the first side wall to a second housing including at least one second side wall defining an internal space and a second opening formed in the second side wall, the connection parts causing one of the first openings to communicate with the second opening,
each of the connection parts including:
a first flange which includes a first through hole penetrating the first flange in a thickness direction and is connected to the second housing when the first through hole faces the second opening; and
an attaching portion which attaches the first flange to the first side wall when the first through hole faces the first opening, and
the attaching portion including at least cane of a first adjuster adjusting an attaching position of the first flange to cause an opposite surface of the first flange, which is opposite to a surface of the first flange facing the first side wall, to be vertical or a second adjuster adjusting an attaching position of the first flange about a horizontal axis which passes the center of the first through hole and extends along the thickness direction,
wherein, each of the connection parts further includes an annular elastic sealing member which is provided between the first flange and the first side wall to surround the first through hole and the first opening, and
the first adjuster includes: a plurality of first screws which are provided around the first through hole of the first flange to determine the upper limit of a separation distance between the first flange and the first side wall within a range of elastic deformation of the sealing member; and a plurality of second screws which are provided around the first through hole of the first flange to adjust the attaching position of the first flange by changing the separation distance so that the opposite surface of the first flange is vertical, the separation distance changed by the second screws being equal to or shorter than the upper limit determined by the first screws.

2. A connection mechanism comprising a plurality of connection parts which connect a first housing including at least one first side wall defining an internal space and a plurality of first openings formed in the first side wall to a second housing including at least one second side wall defining an internal space and a second opening formed in the second side wait the connection parts causing one of the first openings to communicate with the second opening, each of the connection parts including:
a first flange which includes a first through hole penetrating the first flange in a thickness direction and is connected to the second housing when the first through bole faces the second opening; and
an attaching portion which attaches the first flange to the first side wall when the first through hole faces the first opening, and
the attaching portion including at least one of a first adjuster adjusting an attaching position of the first flange to cause an opposite surface of the first flange, which is opposite to a surface of the first flange facing the first side wall, to be vertical or a second adjuster adjusting an attaching position of the first flange about a horizontal axis which passes the center of the first through hole and extends along the thickness direction, wherein, the second adjuster includes: a plate which faces an inner circumferential surface of the first opening and an inner circumferential surface of the first through hole and is attached to the inner circumferential surface of the first opening; and an adjusting screw which is provided to face the inner circumferential surface of the first through hole and adjusts the attaching position of the first flange about the horizontal axis by changing a separation distance between the plate and the inner circumferential surface of the first through hole.

3. A connection mechanism comprising a plurality of connection parts which connect a first housing including at least one first side wall defining an internal space and a plurality of first openings formed in the first side wall to a second housing including at least one second side wall defining an internal space and a second opening formed in the second side wall the connection parts causing one of the first openings to communicate with the second opening, each of the connection parts including:
a first flange which includes a first through hole penetrating the first flange in a thickness direction and is connected to the second housing when the first through hole faces the second opening; and
an attaching portion which attaches the first flange to the first side wall when the first through hole faces the first opening, and
the attaching portion including at least one of a first adjuster adjusting an attaching position of the first flange to cause an opposite surface of the first flange, which is opposite to a surface of the first flange facing the first side wall, to be vertical or a second adjuster adjusting an attaching position of the first flange about a horizontal axis which passes the center of the first through hole and extends along the thickness direction, wherein, the first flange is circular in shape,
each of the connection parts further includes:
a movable member supported by a peripheral end portion of the first flange to be movable along the peripheral end portion; and
a circular second flange which includes a second through hole penetrating the second flange in the thickness direction and is attached to the second side wall of the second housing when the second through hole faces the second opening,
a plurality of protrusions are formed on an outer circumference side face of the second flange to protrude in a direction along the diameter of the second flange,
the movable member includes a protruding portion which protrudes away from the first housing as compared to the opposite surface of the first flange, and
the protruding portion includes a plurality of press portions which are engaged with the protrusions to press the second flange onto the first flange when the movable member is moved along the peripheral end portion while the opposite surface of the first flange faces an opposite surface of the second flange, which is opposite to a surface of the second flange facing the second side wall.

4. The connection mechanism according to claim 3, wherein, each of the connection parts further includes an annular elastic sealing member which is provided between the first flange and the second flange to surround the first through hole and the second through hole.

* * * * *